(12) United States Patent
Connors et al.

(10) Patent No.: US 8,870,856 B2
(45) Date of Patent: Oct. 28, 2014

(54) METHOD FOR HEATING SKIN USING LIGHT TO PROVIDE TISSUE TREATMENT

(75) Inventors: Kevin P. Connors, San Francisco, CA (US); David A. Gollnick, San Francisco, CA (US); Dean A. MacFarland, Magnolia, MA (US); Greg Spooner, Kensington, CA (US)

(73) Assignee: Cutera, Inc., Brisbane, CA (US)

( * ) Notice: Subject to any disclaimer, the term of this patent is extended or adjusted under 35 U.S.C. 154(b) by 511 days.

(21) Appl. No.: 10/789,139

(22) Filed: Feb. 27, 2004

(65) Prior Publication Data

US 2005/0049658 A1     Mar. 3, 2005

Related U.S. Application Data

(60) Provisional application No. 60/540,981, filed on Jan. 30, 2004, provisional application No. 60/497,745, filed on Aug. 25, 2003.

(51) Int. Cl.
| | |
|---|---|
| *A61B 18/18* | (2006.01) |
| *A61B 18/20* | (2006.01) |
| *A61B 17/00* | (2006.01) |
| *A61B 18/00* | (2006.01) |

(52) U.S. Cl.
CPC .......... *A61B 18/203* (2013.01); *A61B 2018/208* (2013.01); *A61B 2017/00199* (2013.01); *A61B 2018/00452* (2013.01); *A61B 2018/1807* (2013.01); *A61B 2018/0047* (2013.01)
USPC .................. 606/9; 606/11; 128/898

(58) Field of Classification Search
CPC .......... A61B 18/18; A61B 2018/1807
USPC .......... 128/898; 606/9; 607/88–94
See application file for complete search history.

(56) References Cited

U.S. PATENT DOCUMENTS

| 1,800,277 | A | 4/1931 | Boerstler | |
|---|---|---|---|---|
| 634,113 | A | 3/1950 | Riley | 81/22 |
| 2,699,771 | A | 1/1955 | Rüttger-Pelli | 128/24.1 |
| 3,327,712 | A | 6/1967 | Kaufman et al. | 128/398 |

(Continued)

FOREIGN PATENT DOCUMENTS

| CA | 968854 | 6/1975 | 326/4 |
|---|---|---|---|
| CA | 1041610 | 10/1978 | 326/16 |

(Continued)

OTHER PUBLICATIONS

Jacques, "Skin Optics"; Oregon Medical Laser Center News. Jan. 1998; http://omlc.ogi.edu/news/jan98/skinoptics.html.*

(Continued)

*Primary Examiner* — David Shay
(74) *Attorney, Agent, or Firm* — Morrison & Foerster LLP

(57) ABSTRACT

A system and method for using a light source to treat tissue with NIR light. The operation provides for generating higher temperatures in deeper layers of tissue relative to higher layers of tissue. The increased temperature in dermal layers can operate to induce collagen shrinkage, or remodeling. One of the light sources for providing a broad spectrum of NIR light is a filament light. The light from the filament lamp can be selectively filtered, and after filtering this light is applied to the skin, where the selective filtering can enhance the ability to elevate the temperature of deeper layers of tissue, relative to layers of tissue which are closer to the surface of the skin.

9 Claims, 9 Drawing Sheets

(56) References Cited

U.S. PATENT DOCUMENTS

| | | | | |
|---|---|---|---|---|
| 3,538,919 A | 11/1970 | Meyer | | 606/36 |
| 3,648,706 A | 3/1972 | Holzer | | 128/395 |
| 3,693,623 A | 9/1972 | Harte et al. | | 128/303.1 |
| 3,834,391 A | 9/1974 | Block | | 606/9 |
| 3,867,948 A | 2/1975 | Kallenborn | | 128/395 |
| 3,900,034 A | 8/1975 | Katz et al. | | 607/89 |
| 4,020,383 A | 4/1977 | Labadini et al. | | 313/344 |
| 4,022,534 A | 5/1977 | Kishner | | 356/210 |
| 4,122,853 A | 10/1978 | Smith | | 606/4 |
| 4,233,493 A | 11/1980 | Nath | | 219/354 |
| 4,298,005 A | 11/1981 | Mutzhas | | 128/396 |
| 4,388,924 A | 6/1983 | Weissman et al. | | 606/9 |
| 4,461,294 A | 7/1984 | Baron | | 606/5 |
| 4,505,545 A | 3/1985 | Salia-Munoz | | 350/321 |
| 4,539,987 A | 9/1985 | Nath et al. | | 128/303.1 |
| 4,608,978 A | 9/1986 | Rohr | | 128/303.1 |
| 4,608,990 A | 9/1986 | Elings | | 128/633 |
| 4,617,926 A | 10/1986 | Sutton | | 606/9 |
| 4,658,823 A | 4/1987 | Beddoe et al. | | 128/396 |
| 4,667,658 A | 5/1987 | Guibert | | 128/24.1 |
| 4,686,986 A | 8/1987 | Fenyö et al. | | 128/396 |
| 4,717,863 A * | 1/1988 | Zeiler | | 315/307 |
| 4,733,660 A | 3/1988 | Itzkan | | 606/9 |
| 4,747,660 A | 5/1988 | Nishioka et al. | | 350/96.25 |
| 4,757,431 A | 7/1988 | Cross et al. | | 362/261 |
| 4,784,135 A | 11/1988 | Blum et al. | | 128/303.1 |
| 4,813,412 A | 3/1989 | Yamazaki et al. | | 128/303.13 |
| 4,819,669 A | 4/1989 | Politzer | | 132/200 |
| 4,829,262 A | 5/1989 | Furumoto | | 330/4.3 |
| 4,860,172 A | 8/1989 | Schlager et al. | | 362/32 |
| 4,884,568 A | 12/1989 | Hahn | | 128/303.1 |
| 4,917,084 A | 4/1990 | Sinofsky | | 606/7 |
| 4,930,504 A | 6/1990 | Diamantopoulos et al. | | 128/395 |
| 4,950,880 A | 8/1990 | Hayner | | 250/201.9 |
| 4,976,709 A | 12/1990 | Sand | | 606/5 |
| 5,000,752 A | 3/1991 | Hoskin et al. | | 606/9 |
| 5,057,104 A | 10/1991 | Chess | | 606/9 |
| 5,059,192 A | 10/1991 | Zaias | | 606/9 |
| 5,139,494 A | 8/1992 | Freiberg | | 606/3 |
| 5,161,526 A | 11/1992 | Hellwing et al. | | 128/395 |
| 5,182,857 A | 2/1993 | Simon | | 30/34.05 |
| 5,207,671 A | 5/1993 | Franken et al. | | 606/9 |
| 5,217,455 A | 6/1993 | Tan | | 606/9 |
| 5,226,907 A | 7/1993 | Tankovich | | 606/133 |
| 5,258,989 A | 11/1993 | Raven | | 372/6 |
| 5,259,380 A | 11/1993 | Mendes et al. | | 607/115 |
| 5,282,797 A | 2/1994 | Chess | | 606/9 |
| 5,290,273 A | 3/1994 | Tan | | 606/9 |
| 5,304,169 A | 4/1994 | Sand | | 606/5 |
| 5,304,170 A | 4/1994 | Green | | 606/9 |
| 5,312,395 A | 5/1994 | Tan et al. | | 606/9 |
| 5,320,618 A | 6/1994 | Gustafsson | | 606/9 |
| 5,336,217 A | 8/1994 | Buys et al. | | 606/9 |
| 5,337,741 A | 8/1994 | Diamond | | 600/8 |
| 5,344,418 A | 9/1994 | Ghaffari | | 606/9 |
| 5,344,434 A | 9/1994 | Talmore | | 607/88 |
| 5,374,265 A | 12/1994 | Sand | | 606/5 |
| 5,397,327 A | 3/1995 | Koop et al. | | 606/17 |
| 5,405,368 A | 4/1995 | Eckhouse | | 607/88 |
| 5,409,479 A | 4/1995 | Dew et al. | | 606/9 |
| 5,425,728 A | 6/1995 | Tankovich | | 606/9 |
| 5,441,531 A | 8/1995 | Zarate et al. | | 607/90 |
| 5,458,596 A | 10/1995 | Lax et al. | | 606/31 |
| 5,474,549 A | 12/1995 | Ortiz et al. | | 606/9 |
| 5,486,172 A | 1/1996 | Chess | | 606/20 |
| 5,511,563 A | 4/1996 | Diamond | | 128/848 |
| 5,522,813 A | 6/1996 | Trelles | | 606/2 |
| 5,527,350 A | 6/1996 | Grove et al. | | 607/89 |
| 5,569,979 A | 10/1996 | Scott et al. | | 313/636 |
| 5,572,091 A | 11/1996 | Langer et al. | | 313/636 |
| 5,591,157 A | 1/1997 | Hennings et al. | | 606/3 |
| 5,595,568 A | 1/1997 | Anderson et al. | | 606/9 |
| 5,611,795 A | 3/1997 | Slatkine et al. | | 606/9 |
| 5,620,478 A | 4/1997 | Eckhouse | | 607/88 |
| 5,660,836 A | 8/1997 | Knowlton | | 424/400 |
| 5,683,380 A | 11/1997 | Eckhouse et al. | | 606/9 |
| 5,735,844 A | 4/1998 | Anderson et al. | | 606/9 |
| 5,755,753 A | 5/1998 | Knowlton | | 607/98 |
| 5,769,844 A | 6/1998 | Ghaffari | | 606/16 |
| 5,769,878 A | 6/1998 | Kamei | | 607/88 |
| 5,782,895 A | 7/1998 | Zarate et al. | | 607/88 |
| 5,807,261 A | 9/1998 | Benaron et al. | | 600/473 |
| 5,810,801 A | 9/1998 | Anderson et al. | | 606/9 |
| 5,814,040 A | 9/1998 | Nelson et al. | | 606/9 |
| 5,820,625 A | 10/1998 | Izawa et al. | | 606/9 |
| 5,830,208 A | 11/1998 | Muller | | 606/9 |
| 5,843,074 A | 12/1998 | Cocilovo | | 606/10 |
| 5,843,143 A | 12/1998 | Whitehurst | | 607/88 |
| 5,849,029 A | 12/1998 | Eckhouse et al. | | |
| 5,860,967 A | 1/1999 | Zavislan et al. | | |
| 5,885,274 A | 3/1999 | Fullmer et al. | | 606/9 |
| 5,919,219 A | 7/1999 | Knowlton | | 607/102 |
| 5,964,749 A | 10/1999 | Eckhouse et al. | | 606/9 |
| 5,989,283 A | 11/1999 | Wilkens | | 607/88 |
| 6,015,404 A | 1/2000 | Altshuler et al. | | 606/9 |
| 6,050,990 A | 4/2000 | Tankovich et al. | | 606/9 |
| 6,080,146 A | 6/2000 | Altshuler et al. | | 606/9 |
| 6,080,147 A | 6/2000 | Tobinick | | 606/9 |
| 6,096,029 A * | 8/2000 | O'Donnell, Jr. | | 606/9 |
| 6,096,066 A | 8/2000 | Chen et al. | | 607/88 |
| 6,120,497 A | 9/2000 | Anderson et al. | | 606/9 |
| 6,168,590 B1 | 1/2001 | Neev | | 606/9 |
| 6,171,332 B1 | 1/2001 | Whitehurst | | 607/89 |
| 6,228,074 B1 | 5/2001 | Almeida | | 606/9 |
| 6,235,015 B1 | 5/2001 | Mead, III et al. | | 606/9 |
| 6,241,753 B1 | 6/2001 | Knowlton | | 607/99 |
| 6,273,884 B1 | 8/2001 | Altshuler et al. | | 606/9 |
| 6,280,438 B1 | 8/2001 | Eckhouse et al. | | 606/9 |
| 6,309,387 B1 * | 10/2001 | Eggers et al. | | 606/41 |
| 6,311,090 B1 * | 10/2001 | Knowlton | | 607/101 |
| 6,319,273 B1 | 11/2001 | Chen et al. | | 607/88 |
| 6,334,074 B1 | 12/2001 | Spertell | | |
| 6,338,731 B1 * | 1/2002 | Laufer et al. | | 606/34 |
| 6,375,672 B1 | 4/2002 | Aksan et al. | | |
| 6,377,855 B1 | 4/2002 | Knowlton | | 607/101 |
| 6,381,498 B1 | 4/2002 | Knowlton | | 607/101 |
| 6,383,176 B1 | 5/2002 | Connors et al. | | 606/9 |
| 6,387,089 B1 | 5/2002 | Kreindel et al. | | 606/9 |
| 6,402,739 B1 * | 6/2002 | Neev | | 606/9 |
| 6,405,090 B1 | 6/2002 | Knowlton | | 607/102 |
| 6,413,253 B1 | 7/2002 | Koop et al. | | 606/27 |
| 6,413,268 B1 * | 7/2002 | Hartman | | 607/94 |
| 6,436,094 B1 * | 8/2002 | Reuter | | 606/9 |
| 6,443,978 B1 | 9/2002 | Zharov | | 607/91 |
| 6,453,202 B1 | 9/2002 | Knowlton | | 607/102 |
| 6,461,866 B1 | 10/2002 | Whitehurst | | 435/325 |
| 6,482,199 B1 | 11/2002 | Neev | | 606/10 |
| 6,485,484 B1 | 11/2002 | Connors et al. | | 606/9 |
| 6,508,813 B1 | 1/2003 | Altshuler | | 606/9 |
| 6,511,475 B1 | 1/2003 | Altshuler et al. | | 606/9 |
| 6,517,532 B1 | 2/2003 | Altshuler et al. | | 606/9 |
| 6,524,329 B1 | 2/2003 | Benedict | | 607/88 |
| 6,558,372 B1 | 5/2003 | Altshuler | | 606/2 |
| 6,558,381 B2 | 5/2003 | Ingle et al. | | |
| 6,569,155 B1 | 5/2003 | Connors et al. | | 606/9 |
| 6,602,275 B1 | 8/2003 | Sullivan | | 607/88 |
| 6,605,080 B1 | 8/2003 | Altshuler et al. | | 606/3 |
| 6,613,040 B2 | 9/2003 | Tankovich et al. | | |
| 6,648,904 B2 | 11/2003 | Altshuler et al. | | 607/96 |
| 6,653,618 B2 | 11/2003 | Zenzie | | 250/221 |
| 6,659,999 B1 * | 12/2003 | Anderson et al. | | 606/9 |
| 6,663,620 B2 | 12/2003 | Altshuler et al. | | 606/9 |
| 6,723,090 B2 | 4/2004 | Altshuler et al. | | 606/9 |
| 6,743,222 B2 | 6/2004 | Durkin et al. | | 606/9 |
| 6,749,624 B2 | 6/2004 | Knowlton | | 607/104 |
| 6,920,883 B2 | 7/2005 | Bessette et al. | | |
| 6,997,923 B2 | 2/2006 | Anderson et al. | | |
| 7,033,349 B2 | 4/2006 | Key | | |
| 7,147,654 B2 | 12/2006 | Baumgardner et al. | | |
| 7,220,254 B2 | 5/2007 | Altshuler et al. | | |
| 7,491,222 B2 | 2/2009 | Holjo et al. | | |
| 2002/0019625 A1 | 2/2002 | Azar | | |
| 2002/0055092 A1 | 5/2002 | Hochman | | 435/4 |
| 2002/0091377 A1 | 7/2002 | Anderson et al. | | 606/9 |

(56) References Cited

U.S. PATENT DOCUMENTS

| | | |
|---|---|---|
| 2002/0128635 A1 | 9/2002 | Altshuler et al. ............ 606/9 |
| 2002/0161357 A1 | 10/2002 | Anderson et al. ............ 606/9 |
| 2002/0173780 A1 | 11/2002 | Altshuler et al. ............ 606/9 |
| 2002/0198575 A1 | 12/2002 | Sullivan ............ 607/88 |
| 2003/0004499 A1 | 1/2003 | McDaniel ............ 606/3 |
| 2003/0023283 A1 | 1/2003 | McDaniel ............ 607/88 |
| 2003/0028228 A1 | 2/2003 | Sand |
| 2003/0032900 A1 | 2/2003 | Ella ............ 601/6 |
| 2003/0032950 A1 | 2/2003 | Altshuler et al. ............ 606/9 |
| 2003/0036751 A1* | 2/2003 | Anderson et al. ............ 606/9 |
| 2003/0045916 A1 | 3/2003 | Anderson et al. ............ 607/89 |
| 2003/0055414 A1 | 3/2003 | Altshuler et al. ............ 606/9 |
| 2003/0057875 A1 | 3/2003 | Inochkin et al. ............ 351/224 |
| 2003/0065313 A1 | 4/2003 | Koop et al. ............ 606/9 |
| 2003/0065314 A1 | 4/2003 | Altshuler et al. ............ 606/9 |
| 2003/0069618 A1 | 4/2003 | Smith, III et al. |
| 2003/0125788 A1 | 7/2003 | Long ............ 607/133 |
| 2003/0130709 A1 | 7/2003 | D.C. et al. ............ 607/88 |
| 2003/0195494 A1 | 10/2003 | Altshuler et al. ............ 606/9 |
| 2003/0199859 A1 | 10/2003 | Altshuler et al. ............ 606/9 |
| 2004/0010298 A1 | 1/2004 | Altshuler et al. ............ 607/88 |
| 2004/0024388 A1 | 2/2004 | Altshuler ............ 606/2 |
| 2004/0034319 A1 | 2/2004 | Anderson et al. ............ 604/20 |
| 2004/0093042 A1 | 5/2004 | Altshuler et al. ............ 607/88 |
| 2004/0143247 A1* | 7/2004 | Anderson et al. ............ 606/9 |
| 2004/0147985 A1 | 7/2004 | MacFarland et al. ............ 607/90 |
| 2005/0049658 A1 | 3/2005 | Connors et al. |
| 2005/0107850 A1* | 5/2005 | Vaynberg et al. ............ 607/88 |
| 2005/0107852 A1 | 5/2005 | Levernier et al. |
| 2005/0143793 A1 | 6/2005 | Korman et al. |
| 2006/0052847 A1 | 3/2006 | Davenport et al. |

FOREIGN PATENT DOCUMENTS

| | | | |
|---|---|---|---|
| DE | 33 47 730 A1 | 7/1985 | ............ A61N 5/06 |
| DE | 3803763 A1 | 8/1989 | |
| EP | 0 565 331 A2 | 4/1993 | ............ A61N 5/06 |
| GB | 2 360 946 A | 10/2001 | ............ A61N 5/01 |
| JP | 4-98795 | 3/1992 | ............ H05B 41/24 |
| JP | 4-322668 A | 11/1992 | |
| JP | 5-329218 A | 12/1993 | |
| WO | WO 86/02783 | 5/1986 | ............ H01S 3/08 |
| WO | WO 89/00871 | 2/1989 | ............ A61B 6/00 |
| WO | WO 95/15725 | 6/1995 | ............ A61B 17/41 |
| WO | WO 96/22813 | 8/1996 | ............ A61N 5/06 |
| WO | WO 97/37723 | 10/1997 | ............ A61N 5/06 |
| WO | WO 98/24514 | 6/1998 | ............ A61N 5/06 |
| WO | WO 98/38933 | 9/1998 | ............ A61B 17/36 |
| WO | WO 98/51235 | 11/1998 | ............ A61F 2/00 |
| WO | WO 99/07438 | 2/1999 | ............ A61F 5/06 |
| WO | WO 99/11324 | 3/1999 | ............ A61F 5/06 |
| WO | WO 00/54685 | 9/2000 | ............ A61B 18/20 |
| WO | WO 00/54685 A3 | 9/2000 | ............ A61B 18/20 |

OTHER PUBLICATIONS

H. Kubota., "Atrial Ablation With an IRK-151 Infrared Coagulator," *Annals of Thoracic Surgery*, vol. 66, No. 1, Jul. 1988, pp. 95-100.

In re U.S. Appl. No. 10/351,981, filed Jan. 27, 2003, by Dean A. MacFarland, entitled: Dermatological Treatment Flashlamp Device and Method, 19 two-sided pages in length.

R.M. Adrian, "Treatment of Facial Telangiectasia Using the VersaPulse® Variable Pulse Width Frequency Doubled Neodymium:YAG Laser: A Case Report," 2 pages in length.

J.C. Allain et al., "Isometric Tensions Developed During the Hydrothermal Swelling of Rat Skin," *Connective Tissue Research*, vol. 7, pp. 127-133 (1980).

R.R. Anderson, "Clinical Use of the Lightsheer Diode Laser System," (reprinted with permission from Harvard Medical School, Mar. 1998) from the website located at http://www.lasertraining.com/med-8.htm, printed Sep. 15, 1998, 5 pages long.

R.R. Anderson et al., *International Advances in Surgical Oncology* (vol. 5), section entitled "Lasers in Dermatology Provide a Model for Exposing New Applications in Surgical Oncology," publisher Alan R. Liss, Inc. (1982), pp. 341-358.

W.F. Coulson et al., "Nonablative Laser Treatment of Facial Rhytides: Animal Study," *Abstract of BiOS '98 Symposium [Cutaneous Applications of Lasers]*, Jan. 24-30, 1998 in San Jose, CA, one page in length.

L. Goldman, "Comparison of the Biomedical Effects of the Exposure of Human Tissues to Low and High Energy Lasers," *Ann. N.Y. Acad. Sci.*, vol. 122, May 29, 1965, 1965, pp. 802-833.

K. Iwasaki et al., (Astract) "Development of Laser Systems for Treatment of Hyperpigmented Skin Lesions," *Publication unknown—entire article is in Japanese except for the Abstract*, revised Mar. 1, 1989, pp. 26-34 (Abstract appears on p. 34).

Brochure by SCITON, "PROFILE™ Combination Long Pulse Erbium and Long Pulse Nd:YAG 1064," website http://www.sciton.com/public/profile.htm, printed Jul. 15, 2003, 2 pages in length.

Chen, S. S. (1998). "Heat-Induced Changes in the Mechanics of a Collagenous Tissue: Pseudoelastic Behavior at 37° C," *Journal of Biomechanics* 31:211-216.

Dover, J. S. et al. (Sep. 1996). "Laser Skin Resurfacing," *Seminars in Cutaneous Medicine and Surgery* 15(3):177-188.

Ross, E. V. et al. (Nov. 1997). "Long-Term Results After CO2 Laser Skin Resurfacing: A Comparison of Scanned and Pulsed Systems," *Journal of the American Academy of Dermatology* 37(5):709-718.

\* cited by examiner

METHOD FOR HEATING SKIN USING LIGHT TO PROVIDE TISSUE TREATMENT

RELATED APPLICATIONS

The present application claims benefit from U.S. Provisional Patent Application Ser. No. 60/540,981, filed Jan. 30, 2004, entitled SYSTEM AND METHOD FOR FLEXIBLE ARCHITECTURE FOR DERMATOLOGICAL TREATMENTS UTILIZING MULTIPLE LIGHT SOURCES, AND FILAMENT LIGHT SOURCE TO BE USED IN COMBINATION WITH THE SYSTEM AND METHOD FOR FLEXIBLE ARCHITECTURE FOR DERMATOLOGICAL TREATMENTS, which is incorporated herein by reference, and the present application claims benefit from U.S. Provisional Patent Application Ser. No. 60/497,745, filed Aug. 25, 2003, entitled OPTICAL DEVICE FOR HEATING SKIN USING NIR LIGHT TO PRODUCE TISSUE SHRINKAGE, which is incorporated herein by reference.

BACKGROUND OF THE INVENTION

Devices using radio frequencies have been reported to be useful in heating skin at depths of a few to many millimeters. Such treatments may produce tissue remodeling or shrinkage, resulting in clinically useful changes in the morphology or appearance of the skin. The RF power can be problematic to apply to skin in that the contact electrode geometries and superficial hydration of the skin can greatly affect the coupling of power into the skin. Attendant complications include superficial burns, uneven application of energy. One reference which discusses the uses of a device for applying radio frequency to the skin is U.S. Pat. No. 6,453,202 U.S. Pat. No. 6,453,202, entitled Method and apparatus for controlled contraction of collagen tissue Some prior system have provided for a combination of a light source in combination with use of RF electrodes to obtain relatively deep heating of dermatological issue. Additionally, some efforts have been directed toward developing systems utilizing a filament light source to apply light energy to the skin to achieve collagen shrinkage. However, prior systems have exhibited different significant limitations.

BRIEF DESCRIPTION OF THE DRAWINGS

FIG. 9 illustrates the driving of a filament light according to an embodiment herein.

DESCRIPTION OF THE INVENTION

One embodiment herein provides a number of advantages over some prior systems, such as no electrical contact with patient and reduced sensitivity to surface hydration. Also using a relatively broadband light source allows for tailored spectral profiles by filtering. Further, an embodiment herein provides for a broadband spectrum light source, which can be driven to output a range of different treatment fluences, and allows for control of the skin temperature to reduce the risk of unwanted thermal injury.

The device herein can use an incandescent lamp with significant optical output in the near-infrared range (NIR) from around 750 nm to 3000 nm. The lamp can be a quartz-tungsten-halogen lamp ("QTH"), but other, longer wavelength lamps may be useful (e.g. ceramic or carbon elements). A housing serves to couple NIR light to skin. The lamp is driven with high current supply, and could potentially utilize a modified version of the high voltage power supply described in the pending patent application filed Jan. 27, 2003 DERMATOLOGICAL TREATMENT FLASHLAMP DEVICE AND METHOD, U.S. application Ser. No. 10/351,981, which is incorporated herein by reference.

Figure 1:
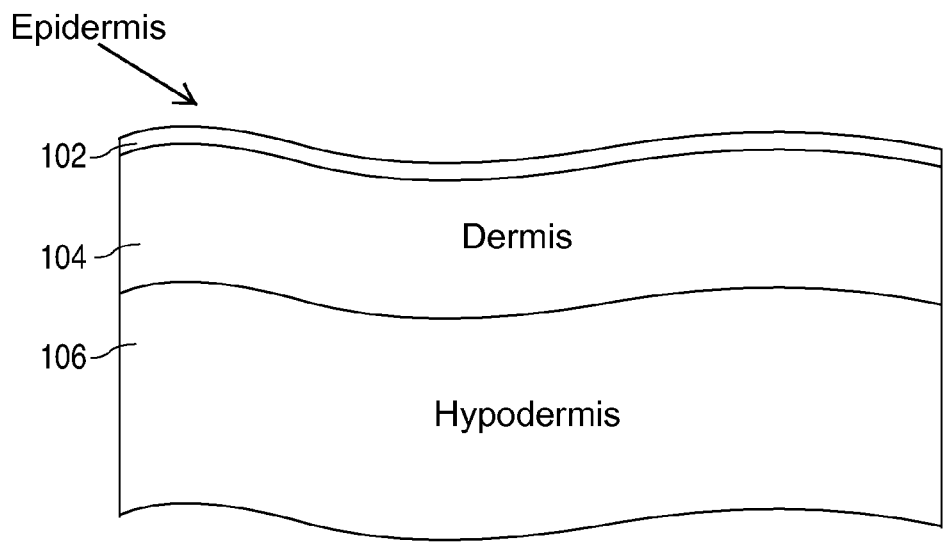
FIG. 1 shows a view of dermatological tissue.

The desired skin absorbance profile is largely determined by water-based absorption in the NIR range, because the dermal layers targeted are generally located 1 to several mm deep. FIG. 1 shows a cross sectional view of dermal tissue. Layer 102 corresponds to epidermal tissue which has a thickness of approximately 100 µm, and this thickness can vary from patient to patient, and depending on the area of skin being treated. Layer 104 corresponds to the dermal layer which can have a thickness in the range of 1-5 mm, and this thickness can also vary from patient to patient, and depending on the area being treated. Layer 106 is the hypodermis. One aspect of the treatment herein is to provide for the heating of water molecules in the dermatological tissue being treated. This heating of the water molecules, will in turn heat adjacent tissue and where the temperature of the tissue reaches approximately 50° C. or above, thermal damage to the tissue can be observed. One aspect of the operation of the system and method herein is to heat collagen, which is a protein that makes up much the dermatological tissue, to a temperature in excess of 50° C. One of the effects of sufficiently heating the collagen, is to cause the collagen to change its characteristics as a result of thermal damage. This changing of the collagen characteristics is sometimes referred to as a shrinkage of the collagen, or remodeling, and this shrinkage of the collagen, can result in the reduction of wrinkles, or what appears to be a general tightening of the skin, in the area where the collagen has been sufficiently heated.

In general, different effects due to collagen shrinkage can be achieved by controlling the temperature profile in tissue being treated. In some circumstances a treatment may target both relatively shallow skin tissue, including possibly tissue in the epidermal layer, and to also heat deeper tissue in the dermal layer. In some other circumstances the treatment can be targeted at heating the dermal layer in the range of 1-6 mm, while minimizing the heating the upper dermal layer and the epidermal layer. Regardless of the specific treatment, it is generally desired to provide for some relatively deep tissue heating in the dermal layer.

To produce deep tissue heating and potential remodeling, or collagen shrinkage, a relatively large volume of skin must be heated. Associated thermal relaxation times are measured in 100 s to 1000 s of milliseconds. Existing art using lamps to heat skin is largely limited to volumes relaxation times below 1000 ms. Thermal relaxation time for deep bulk skin heating will allow exposures >1 second, and in general to deposit sufficient NIR energy, exposure times will be >1 second. Thus, as recognized herein a device may then be turned on for as long as several seconds to produce the desired thermal profile, said profile is based on the knowledge that tissue held at temperatures above 50° C., and preferably above 60° C., for any significant length of time will experience thermal damage, and in the case of collagen this thermal damage can result in remodeling or shrinkage.

A simple calculation provides a rough illustration of the heating required to produce collagen-changing temperatures. For this calculation consider a cylindrical slug of water 3 mm thick and 6 mm diameter and having a thermal relaxation time of approximately 10 seconds. So, heating such a volume could happen more or less adiabatically in a second. If the goal is to pre-heat skin (water) by 20 C in this time, this volume of water (approximately 0.1 cm3) would require (20 C)(4 J/C*cm3)(0.1 cm3)=approx. 8 J. That is 8 J/1 sec=8 watts. Assume the electrical to delivered optical efficiency of the light source is 5%, then 160 watts of electrical power is required. To obtain this efficiency, the source can be smaller in its dimensions (e.g. width) than the treatment snot size (which is approximately 6 mm in diameter). So, if it is a filament, it would ideally have a minimum electrical rating of at least 200 watts and be only a few mm in size.

In one embodiment, a source delivering peak powers in the NIR between 10 and 100 W per cm$^2$ is therefore required. Many generally available 600-1000 W quartz-tungsten-halogen lamps operated at rated power are unlikely to be useful as direct sources, since typical power densities at the lamp envelope are on the order of ~1000 W/20 cm^2=50 W/cm^2, with the power density or irradiance falling rapidly with distance. The NIR portion of this results in power-in-band densities at the envelope in the low 10's of W/cm^2. Getting higher power densities can be achieved through utilization of different possible techniques. One possibility is using a filament light source for a limited life of operation and overdriving the filament lamp. Another option, which could be used alone or in conjunction with overdriving the filament lamp is collecting the output light from the entire envelope filament lamp and directing it to skin by means of a reflector. Another option which could be used in combination with the above options, or alone, is employing water cooling of the quartz envelope of the lamp to enable the use of smaller lamp envelopes.

Light sources other than filament light sources could also be used, but one of the challenges is finding an economical light source that outputs light of spectrum which is useful for heating water, or more specifically for outputting light across desired parts of the NIR range. For example, it is known that Nd:YAG laser light penetrates too deeply to effectively heat water in skin at appropriate depths to perform skin remodeling. The effective penetration depth is a function of the reduced scattering coefficient and the absorption strength of (mainly) water in skin. It is desirable to use somewhat more shallow penetrating light by seeking a waveband in which absorption is somewhat stronger than 1064 nm in water and in which scattering is no greater than the 1064 nm wavelength in skin. Light falling between 950 and 1400 nm has an absorption depth in water that varies between 1 and 28 mm. Taking into account scattering in a simple model, the effective penetration of NIR light in skin in this wavelength range varies from approximately 0.3 to 2.0 mm. Filtering the NIR light produced by a filament lamp can result in an effective penetration depth (function of scattering length and absorption depth) that can be tailored to aid in creating a desired thermal depth profile in tissue being treated. However, no matter what the spectral shape may be, the light intensity in tissue, and the absorption and temperature profiles can only have a shape that is a sum of decaying exponential curves, since the absorption characteristic of each wavelength in skin follows a Beer's Law like profile. The consequence is that the thermal profile has the same basic shape, and that the spectral profile can only alter the general depth and strength of a Beer's Law-like thermal profile.

Useful bands for providing thermal remodeling can include 1150-1400 nm, and perhaps 1500-1850 nm, and in fact light up to 3000 nm range can be beneficial. In the former, scattering is somewhat reduced with respect to 1064 nm light in water, and the absorption depth in water is deep to moderate, ranging from 4-12. Considering the optical penetration depth that applies in skin, including the effects of scattering, the actual depth of penetration is approximately 3 mm. In the latter, scattering is significantly reduced compared to 1064 nm in water, and the absorption depth is relatively shallow (1-2 mm). Light from 1350-1550 nm is strongly absorbed and will only contribute to relatively deep epidermal heating.

In one mode of treatment the desired result is to produce higher temperatures in deeper thermal layers relative to the temperature at the epidermis. Heat is primarily deposited in a Beer's Law type profile, which subsequently transfers heat to the bulk of the skin. Absent some cooling applied to the surface of the skin, the application of light energy would generally be higher in the epidermis than in the dermis.

Figure 2A:
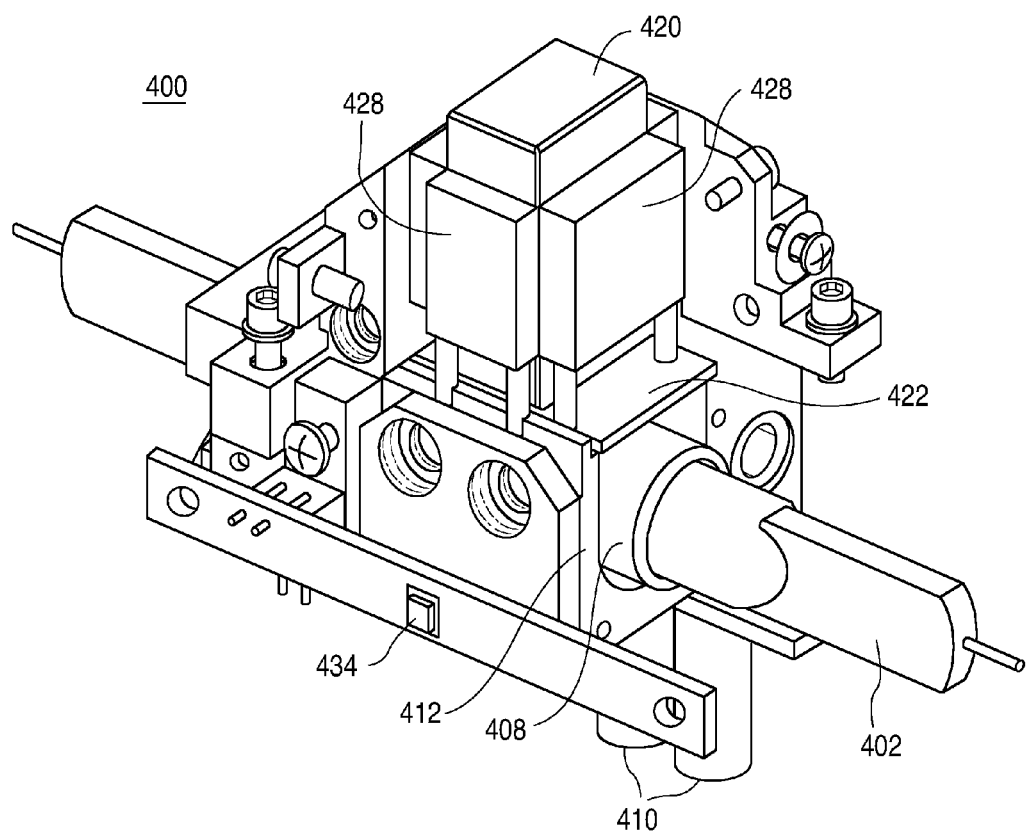
FIGS. 2a-2b show views of an embodiment of a system herein.
Figure 2B:
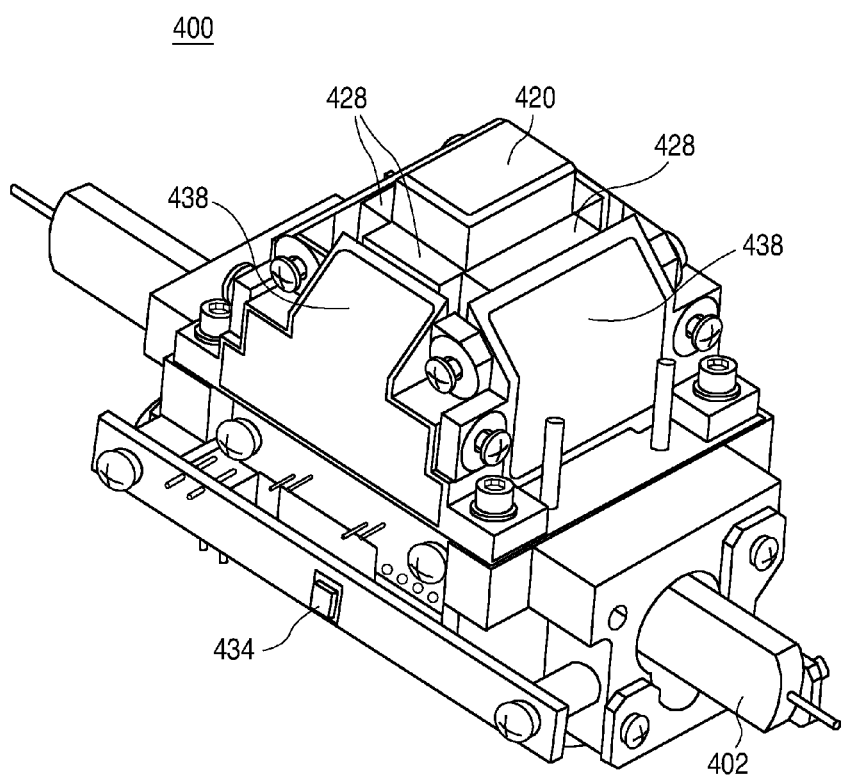
Figure 3A:
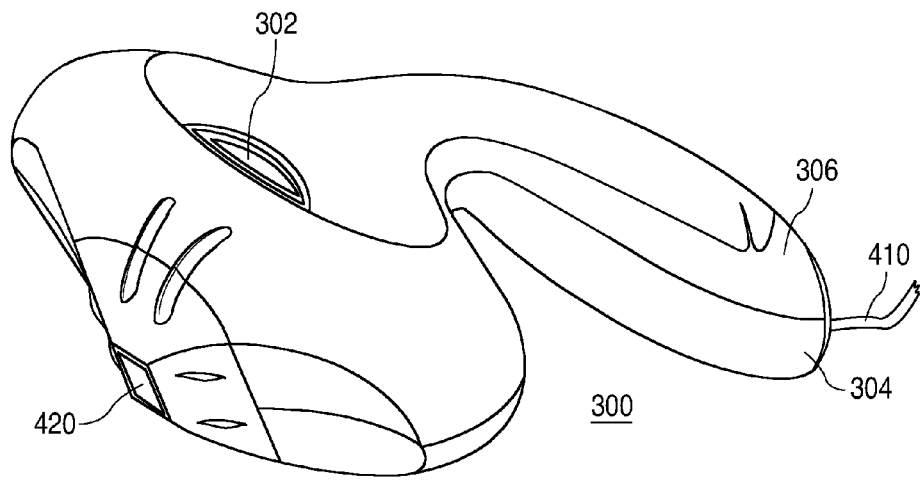
FIGS. 3a-3b show views of an embodiment of handpiece of a system herein.
Figure 3B:
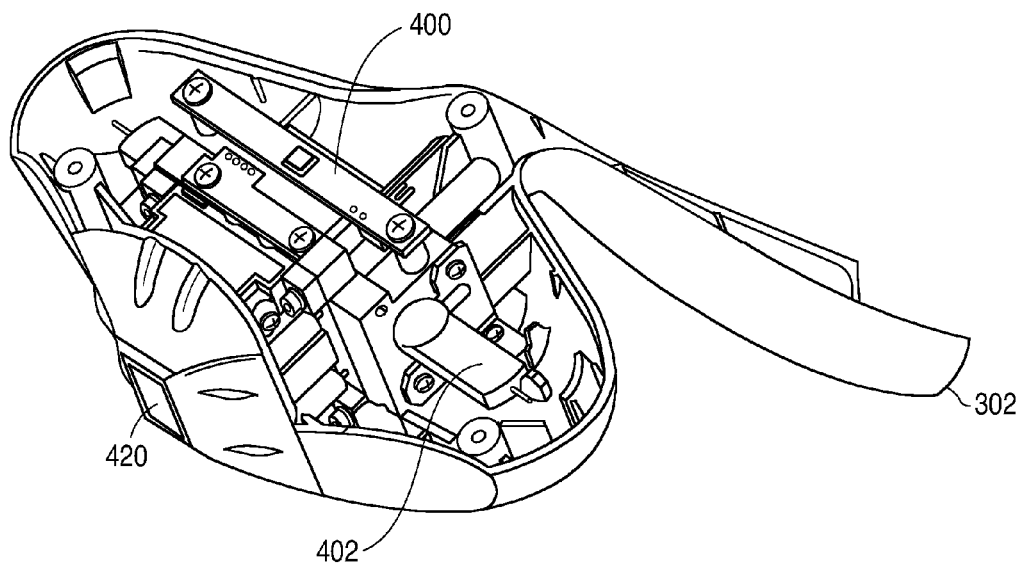
Figure 4:
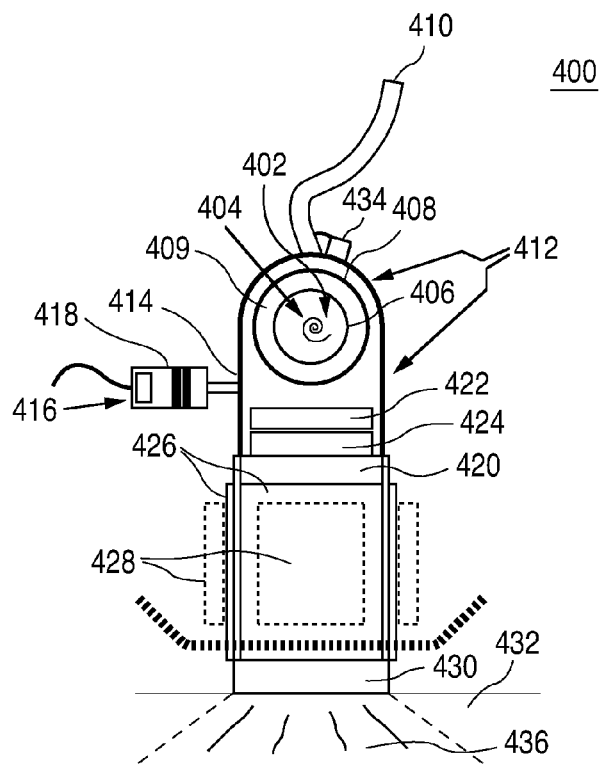
FIG. 4 shows a cutaway view of an embodiment of a system herein.

FIGS. 2a-2b and FIG. 4 illustrates aspects of a filament lamp system 400 of an embodiment herein which can be used to deliver NIR light to tissue to provide treatment exposures. FIG. 3 shows an ergonomic handpiece 300 in which the filament lamp system 400 is disposed. FIG. 2a shows a view of the filament lamp system 400 with some of the elements removed so as to be able to view elements in the system 400. FIG. 2b shows a view of an assembled filament lamp system which would be disposed in the handpiece 300. In reviewing the FIGS. 2-4. Common reference numbers have been used to identify elements, where the same element is shown in various views represented by the figures. FIG. 4 shows a simplified cutaway view of the filament lamp system corresponding to FIG. 2a. The function of the filament lamp system is described in detail in connection with FIG. 4 below. However, a brief discussion of FIGS. 2a-2b, and FIGS. 3a-3b is provided initially to give an overview of the system.

FIG. 2a shows the system 400 the system 400 includes a filament lamp 402, and surrounding the filament lamp is a flow tube 408. A housing is 412 is provided, and light from the filament light is transmitted through other optical components such as a filter 422 and a sapphire block 420. The sapphire block 420 is cooled using thermoelectric coolers 428. The system also includes an LED 434 to indicate when tissue is being treated. FIG. 2b corresponds to FIG. 2a, but shows additional copper cooling blocks 438 secured against the thermoelectric coolers 428. These cooling blocks 438 can be supplied with cooling fluid, which operates to dissipate heat generated on the outer walls of the thermoelectric coolers 428.

FIGS. 3a-3b illustrate an embodiment of an ergonomic handpiece 300 with the filament light system disposed therein. The handpiece can consist of molded plastic pieces, or other suitable material. As shown the handpiece 300 has two molded plastic pieces 304 and 306. A cavity is formed between the molded plastic pieces, and the filament lamp system 400 is disposed in this cavity. Two apertures are providing the handpiece. One aperture is covered with a lens 302 through with light from the LED 434 is transmitted. The second aperture allows the sapphire block 420 to protrude from the handpiece so that it can be pressed against the skin. Epoxy can be applied to the seam between molded plastic pieces and the sapphire block to improve the seal between the sapphire and the plastic.

FIG. 4 shows a simplified cut away view of the system. The system includes a filament lamp 402. This filament incandescent lamp is an incandescent light source, and includes a filament 404. The filament lamp includes a quartz tube 406 in which a gas is disposed. In one embodiment the quartz tube 406 has a diameter of 10 mm. The length of the filament itself is approximately 22 mm, while the overall length of the lamp is approximately 4 inches. In order to obtain the desired light output the filament can be of a diameter of approximately 0.75 mm, and formed in to a helical shape having approximately 7 turns. The quartz tube 406 of the filament lamp is disposed within a flow tube 408 which can be formed with a transparent material such as glass or Pyrex. A fluid such as water is disposed within the cooling annular region 409 between the flow tube 408 and the quartz the 406. This water can pumped through the annular flow region 409 by a pump and cooling system. In one embodiment the diameter of the flow tube 408 is 11 mm. Thus, the annular flow region 409 provides a spacing of approximately 0.5 mm between the outer wall of the quartz tube 406 and the inner wall of the flow tube 408. The water disposed in the flow region 409 can serve two purposes. One purpose is to cool the filament lamp. Given the relatively high power of the lamp, in one embodiment the filament lamp has an electrical rating of 400 W, and the small diameter of the lamp, and the confined geometry of the handpiece, traditional air cooling of the filament lamp is not possible. A second function of the water is to filter out some of the wavelengths of light generated by the filament lamp (through absorption). The amount of light filtered can be varied by providing flow tubes 408 with different diameters. In one embodiment different interchangeable handpieces could be provided where the systems disposed in the handpieces provide different thickness for the water envelop in the annular flow region 409. As the thickness of the water, which forms an envelop around the lamp is increased, the light transmitted through water will be subject to more absorption in the water, and thus less of the light at wavelengths which are absorbed by water will be transmitted through the flow tube 409. An umbilical connector 410 will transmit electrical power and coolant fluid to the system 400.

The filament lamp and the flow tube are disposed in a housing 412. The housing can be formed of a metal such as aluminum. The inner wall of the of the housing can be coated with a highly reflective metal, or it could be highly polished aluminum. In one embodiment a highly reflective gold coating is provided, where gold is used because it is highly reflective for NIR light. The housing is provided with a small aperture 414 which allows for a photodetector 416 to be disposed such that it can sense the light output power transmitted by through the flow tube 408. Depending on the sensitivity of the photodetector, and the output power, the photodector can be provided with an attenuator 418. The reflective housing is coupled to a sapphire block 420. A filter 422 can be provided such that additional undesired light can be filtered out prior to transmitting light from the reflective housing 412 into the sapphire block 420. In one embodiment the filter 422 is a non absorbing NIR and IR transmitting wavelength filter. The interface between the filter 422 and the sapphire block 420 is provided with an anti reflecting coating on the surface of the sapphire block to minimize power loss which can occur as light is transmitted through the filter 422 into the sapphire block. The lateral sides of the sapphire block 420 can be coated with metal surfaces 426. These metal surfaces should be as reflective as possible to minimize losses as the light is transmitted through the sapphire block. It should be recognized that an embodiment of the system might be implemented without the metal coating on the sides, and the total internal reflection of the sapphire block could suffice, so long as other elements were not in direct contact with the sapphire block. In one embodiment the metal used is Aluminum, as this metal has reasonably good reflective properties and easily adheres to the surface of the sapphire block. A cooling system is provided to control the temperature of the sapphire block, and the system can use thermoelectric coolers disposed on the metal surfaces 426. These thermoelectric coolers 428 operate to control the temperature of the sapphire block 420. The operation of thermoelectric coolers, which is known in the art, is such that by application of the electrical current to the thermoelectric cooler, one side of the thermoelectric cooler can be made cooler, while the other side of the thermoelectric cooler becomes hotter forming an electrically driven heat pump. In the embodiment shown, the cool side of the thermoelectric cooler is adjacent to the sapphire block. Additionally, although not shown in FIG. 4, cooling fluid can be used to remove heat from the side of the cooler which is not adjacent to the sapphire block 420. The sapphire block could be replaced with a block of different material, which would form a lightwave guide. Sapphire is, however, a desirable material for the system as it is a good transmitter of light, and it is also a good conductor for heat. In operation the outer surface 430 of the sapphire block is pressed against the area of the patient's skin 432 which is to be treated. The light 436 from the filament lamp is then transmitted into the patient's skin.

Figure 10:
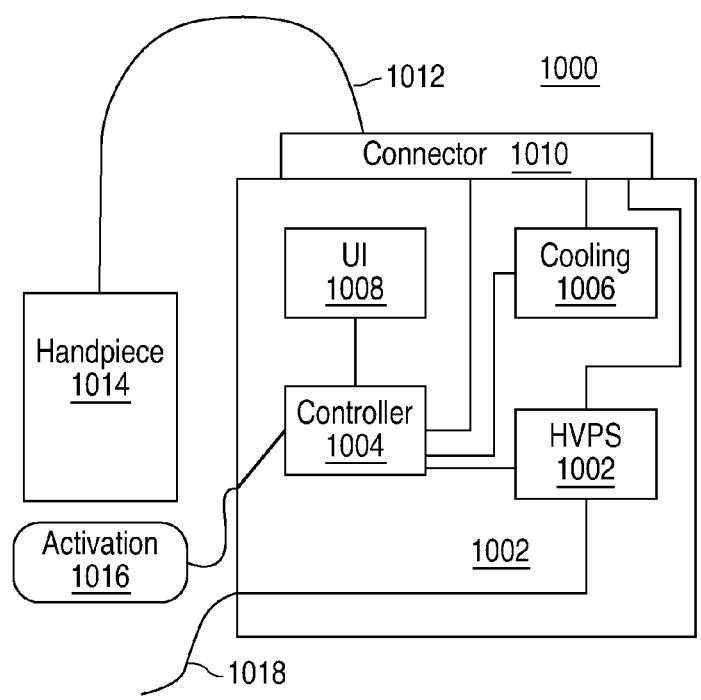
FIG. 10 illustrates an embodiment of a system herein.

As discussed above the umbilical cable connects to the lamp system to provide control signals, electrical power and cooling fluid to the system 400. FIG. 10 provides a view of an embodiment of a system 1000 herein. As shown the system 1000 includes a main console 1020. Although the main console is shown as a single unit, it could in fact be multiple components connected together. The main console includes a controller 1004 which controls the overall operation of the other components of the system 1000. A power cord 1018 is provided to receive AC power, a power supply which can include a HVPS supply for driving the filament lamp provides power to elements of the system 1000. The main console also includes a user interface. In one embodiment this user interface 1008 is a touch screen display, and the controller is operable to drive the user interface 1008 to display different screens where a user can input treatment parameters. A cooling system which controls the temperature and flow of fluids which are used to control the temperature of components in the hand piece 1014. The power for driving the flashlamp, control signals and cooling fluids are delivered to the hand piece via the umbilical cable 1012. The umbilical cable is connected to the main console via a 1010. This connector, can include multiple connectors to allow for multiple hand pieces to be connected to the main console at different times. The controller operates to recognize the handpiece which is selected by a user, and to provide appropriate user interfaces and controls the selected hand piece which is being used to apply a treatment. An activation switch 1016 such as a foot pedal is provided so that a user can initiate the driving of the light source by stepping on the foot pedal.

Figure 5:
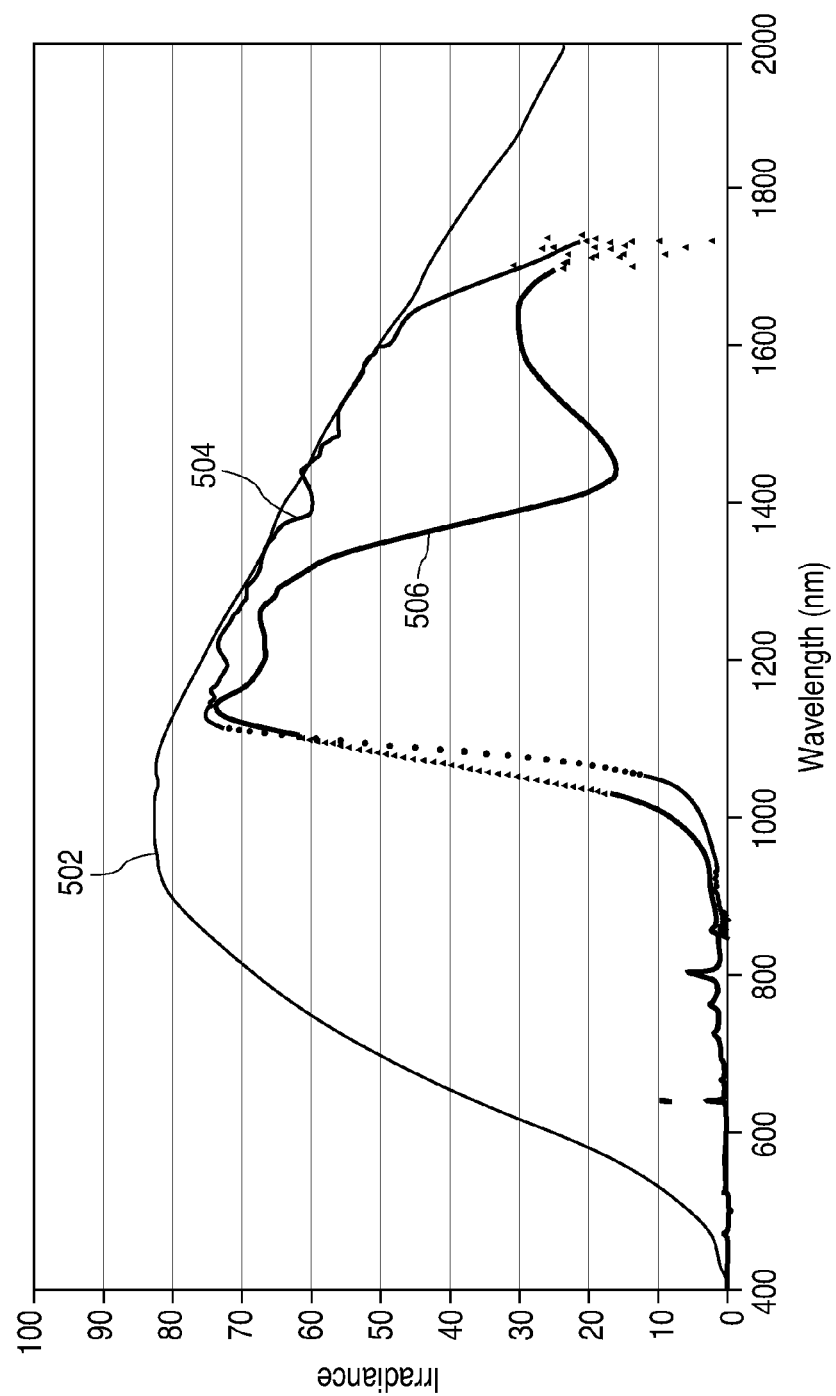
FIG. 5 shows a graph illustrating filtering of a broadband spectrum, according to an embodiment herein.

FIG. 5 illustrates aspects of the operation of the system 400. The trace 502 shows an approximation of optical spectral power which is generated by the filament lamp without any filtering. As is known a quartz-tungsten-halogen filament lamp outputs a broad light spectrum approximating a black body radiation. By using a relatively heavy gauge tungsten filament the amount of NIR light can be increased over thinner gauge filaments, for a fixed input power. This is because the temperature that the radiating filament operates at for the input power is lower for larger gauge wires, and as is known the radiation temperature determines in large part the spectral curve. In order to achieve deep dermal heating for example up to approximately 4-6 mm, without damaging or burning the more shallow epidermal layers of the skin it is advantageous to filter out wavelengths of the spectrum which could be absorbed by more shallow layers of skin. The filter 422 operates to filter out light in the spectrum below approximately 1050 nm. The trace 504 shows the effect of filter 422 on the light generated by the filament lamp. It should be noted that the rapid follow off of the power in trace 504 at approximately 1750 nm, is not in fact due to the filter 422, rather it is a limitation of the IR detector array used to measure the power output the filament lamp and in reality trace 504 would approximate the upper end of the trace 502. Trace 506 shows the irradiance of the light output where the filter 422 is filtering light below 1050 nm, and the water in flow tube is operating to filter out some of the light which is strongly absorbed by water. At approximately, 1450 nm, where water absorption coefficient of water is very strong, it can be observed that a large amount of the irradiance from the flash lamp is filtered out. It should be noted the shown rapid fall off of trace 506 at approximately 1750 nm is due in large part to the limitations detector used to measure the power, and in fact a more gradual decrease in the power would be present above 1750 nm. Depending on the desired treatment, systems providing for a thicker or narrower water envelop around the quartz tube of the filament lamp can be used. Where heating of shallower layers of the dermis, or possible parts of the epidermis is desired the thickness of the water envelop can be reduced by, for example, using a smaller diameter flow tube. This will result in less absorption, or filtration of light by the coolant water in the range of 1450 nm, and this light energy which is not filtered would then be absorbed in the shallower layers of the dermis and the epidermal layer. Where deeper heating is desired, then it can be beneficial to increase the absorption of the light in the range of 1450 nm to reduce the absorption of this energy in the shallower layers in the skin. This allows for ability to keep the more shallow layers of the skin relatively cool, in part by reducing the light energy which would be absorbed in the more shallow layers of tissue. This reduction of the light which would be absorbed in the more shallow layers, and the cooling of the sapphire window to dissipate heat in the shallow layers of the dermis and epidermis, while still providing light energy that will propagate to deeper layers of the dermis, enhances the desired result of heating the deeper layers of tissue relative to more shallow layers of tissue.

Figure 6:
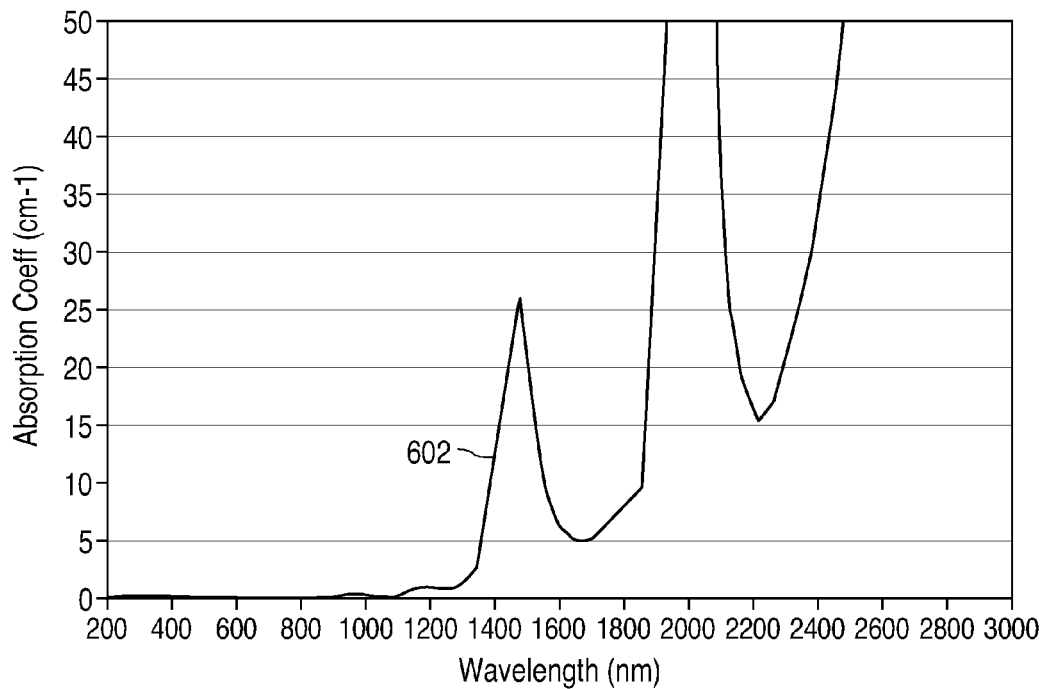
FIG. 6 is a graph illustrating the absorption coefficient of water.
Figure 7:
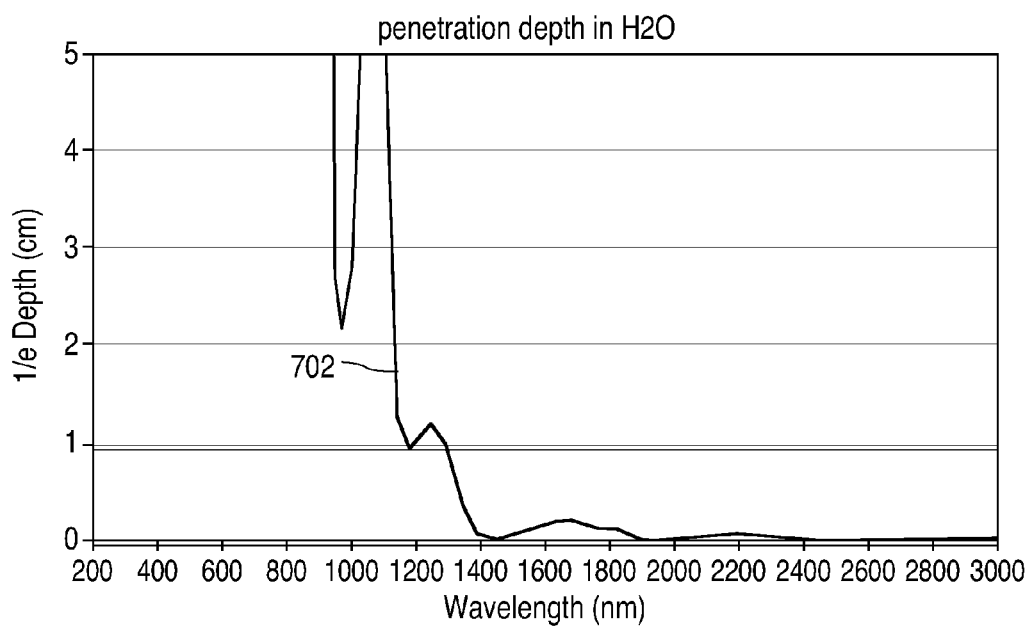
FIG. 7 shows a graph illustrating the penetration of different wavelengths of light in water.

FIG. 6 shows a graph with a trace showing the absorption coefficient of water. As would is expected based on the discussion of FIG. 5, water has as very strong absorption coefficient at approximately 1450 nm. FIG. 7 shows a trace 702 that corresponds to the depth of light penetration into water. This graph illustrates that by filtering out light in the range of 1450 nm and at wavelengths above 1850 nm much of the energy which would be absorbed by the water in the shallow layers of the dermis or epidermis is be removed.

Figure 8:
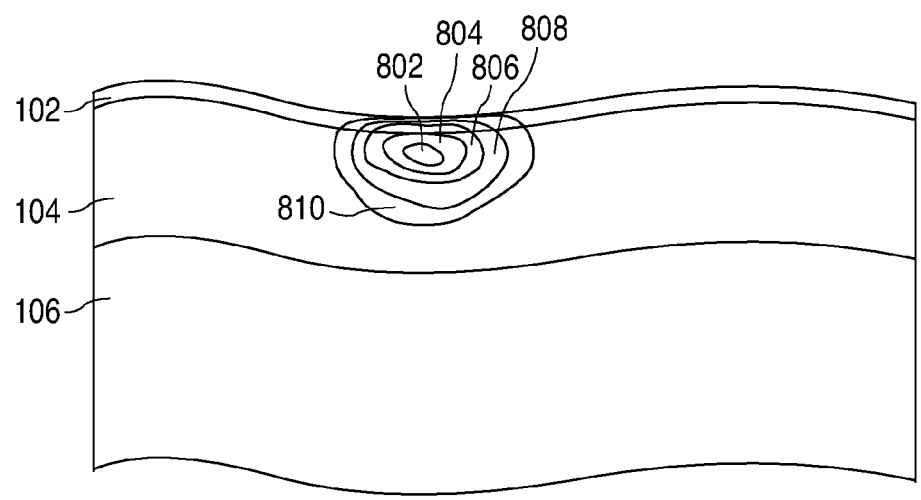
FIG. 8 illustrates an example of a thermal profile in tissue being treated.

FIG. 8 shows an idealized view of the temperature profile in dermatological tissue where an exposure treatment has been applied using a system and method herein. The goal of one treatment herein is to provide for heating in regions 802 and 804 to approximately 60° C. while regions 806 and 808 and 810 remain at much cooler temperatures due to the active cooling of the sapphire block and the filtering out of light which would be absorbed in the shallow layers of the dermis and epidermis. In one mode of treatment regions 802 and 804 would be in the depth range relative to the top surface of the tissue of approximately 1-4 mm.

To achieve the type of tissue heating described above consideration must be given to the temperature of the sapphire block and the driving of the filament lamp. When a user has activated the filament hand piece, by for example stepping on the activation switch 1016, the controller and power supply coupled to the filament lamp hand piece by the umbilical cable are activated to provide a treatment. In one embodiment the user will be able select an amount of fluence for a treatment exposure using the user interface 1008. Once the user has selected an amount of fluence, the controller will determine how long the filament light source will be activated to generate light to output the desired fluence. The system is designed to provide a fluence range of from 10 J/cm2 to 50 J/cm2. Of course these amounts could be modified if desired. Once the user has selected the desired amount of fluence, the hand piece 1014 is positioned so that the sapphire window is against the area of skin to which the exposure is to be applied. The user can then step on an activation pedal which will cause the treatment to begin. Upon stepping on the activation pedal, an LED 434 will light to indicate that the treatment has begun and that the user should not remove, or move, the handpiece and sapphire window relative to the area of patient's skin being treated. Initially, the system will operate to apply electrical current to the thermoelectric coolers and the temperature of the sapphire block will be brought to a treatment temperature. In one embodiment the treatment temperature is 20° C., but this could be set to a different temperature. The cooled sapphire block will continue to be pressed against the patient's skin for the initial cooling period where the sapphire will operate to cool the surface of the patient's skin. In one embodiment this initial cooling period will last for period of approximately 1 second. After approximately 1 second the power supply will operate to provide electrical energy to the filament of the filament lamp for a period of time until the desired fluence as been delivered to the patient's tissue. Depending on the desired fluence light will be transmitted from the filament to the patient's skin for a period of time ranging from slight more than 1 second, an appropriate minimum could be for example around 1.2 seconds, and an appropriate maximum could be around 5 seconds. As will be discussed in more detail below, the power supply will stop applying electrical current approximately 1 second prior to the end of the treatment exposure and the hot filament light will continue to emit light until it has cooled sufficiently. The amount of time for which the filament radiates after current application is stopped depends on the thermal mass of the filament and the operating filament temperature, and can range form 0.1 to 2 seconds. During the application of the light from the filament lamp, the cooling system including the thermoelectric coolers will continue to cool the sapphire block, ideally keeping the temperature at the initial treatment temperature. After the filament light has stopped outputting the treatment exposure, the cooling system will continue to cool the sapphire block for a post treatment exposure time period, and the sapphire block will operate to dissipate heat from the patient's skin. The LED 434 will remain lit through the initial cooling time, the time when the treatment exposure is being applied, and through the post cooling time period. By keeping the LED lit, the user will know not to remove the hand piece and the sapphire block until the treatment exposure has concluded, and the post cooling time period has ended. In addition to the LED turning off to signal the end of a treatment, an audible signal could be provide to indicate to user that a treatment has been completed.

Figure 9A:
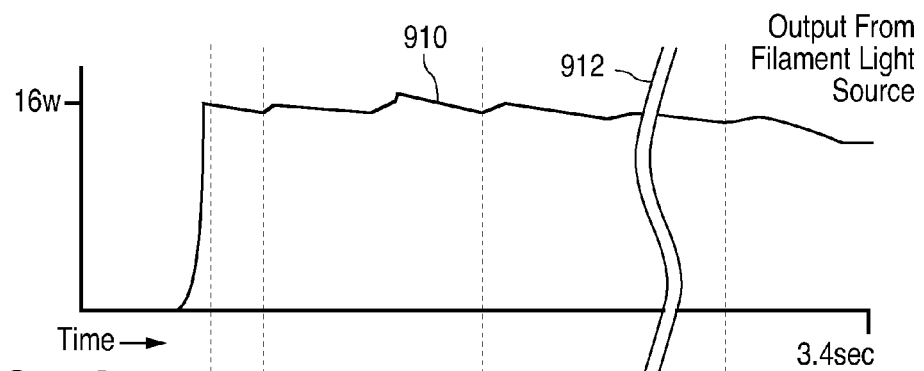
FIG. 9A is a plot of light power output as a function of time.
Figure 9B:
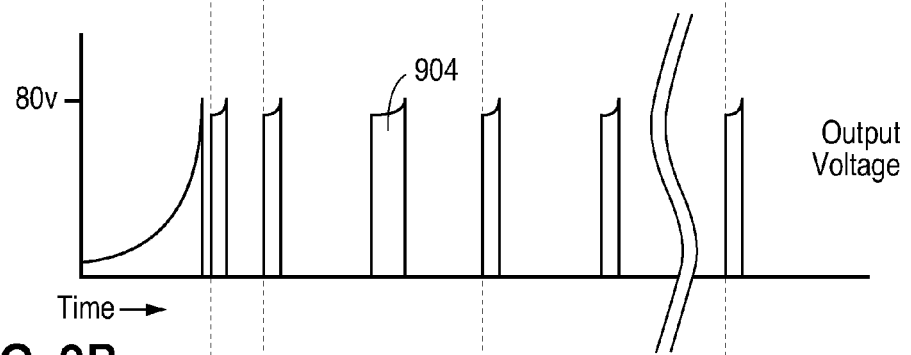
FIG. 9B is a plot of voltage output as a function of time.
Figure 9C:
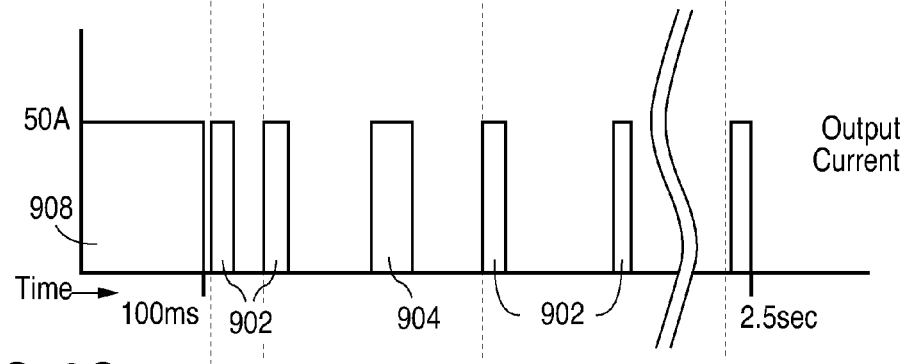
FIG. 9C is a plot of current output as a function of time.

FIG. 9 shows an example of the current and voltage used in driving the filament lamp. In driving the filament lamp, pulses of electrical current are used to drive the filament of the filament lamp. FIG. 9C shows the current output for driving a filament light source FIG. 9A shows the corresponding power output 910 detected by the photodetector which senses the power in the housing. FIG. 9B shows the output voltage. In this example a filament light source would be driven with an initial pulse 908 of electrical current having duration of 100 ms, and a current amplitude of 50 A, and then subsequent pulses 902 and 904 of electrical current. Depending on the desired operation of the system pulse widths of a wide range of different widths could be used, and the frequency of the pulses could be increased or decreased. The long initial pulse 908 is used to initially heat the filament light source, and rather than using one relatively long pulse a series of shorter closely spaced pulses could be used. Pulses 902 show 0.5 ms pulses and 904 shows a 1 ms pulse, the duration between pulses can be varied based on a signal from a photodetector which senses the optical output power, and/or based on a voltage sensed across the lamp. In one embodiment for example the applied electrical pulse would be such the output of power from the filament light would be ±1.5% of 16 watts. Thus, when the photodector sensed the power output dropped to a threshold level a 0.5 ms pulse of 50 A would be applied to the filament light source. As shown in FIG. 9 each pulse of current would have result in a corresponding voltage applied to the filament light source. The system can operate such that toward the end of a 0.5 ms pulse, based on a sensed optical output power, or a sensed voltage across the lamp, a subsequent 0.5 ms pulse can be applied if the optical power or voltage has not reached some threshold value. Voltage pulse 914 and current pulse 904 illustrate a situation where two 0.5 ms pulses are applied to form a single 1.0 ms pulse. Of course a wide range of different approaches could be used to drive the filament lamp to output the desired power. The output power from the filament light source is shown in FIG. 9 as detected by a photodetector as curve 910. The area 912 is a break in the time line, during which additional pulses would continue to be applied to the filament light source. The operation of the filament light source is such that it will continue to output electromagnetic energy for so long as the filament remains sufficiently hot. Thus, the curve 910 shows that optical power continues to be output by the filament light source even after the pulses of electrical current are no longer being supplied to the filament light source. In the example, shown in FIG. 9 for example where the last electrical pulse is applied at 2.5 seconds, the filament light source would continue to output a significant amount of output power up to about 3.4 seconds.

The filament can also be driven continuously by a supply, it is not a requirement to pulse the filament current at intervals during the treatment. This was actually a method developed to obtain filament capability using the same power supply that drives flashlamps. Other variations and different methods could be utilized such as providing a higher current during the preheat phase of the pulse, in order to bring the lamp up to heat quickly. This could be combined into one long pulse with higher current in the beginning and lower current at the end. An alternate control method would be to control the voltage applied to the lamp. The voltage would ramp up at a controlled rate to limit the inrush current. Alternately the voltage control would be a step applied and the current limit of the supply would limit the current.

The above described operation of the power supply driving a filament light source, illustrates an aspect of an embodiment of the present system. Specifically, a filament light source is normally considered a relatively low current, low voltage device. However, the filament light source can be driven with the same power supply which is used to supply high current and high voltage that is required to drive a flashlamp. As describe above the ability to control the power supply to short pulses of relatively high current, allows for the controllable power supply to drive the filament light source in a manner for providing effective treatments.

In another embodiment of the system herein, the filament lamp could be driven with lower current power supply which would apply a more continuous, but lower amplitude current to drive the filament. As one of skill in the art will recognize a variety of different power supplies could be used to drive the filament lamp.

Figure 11:
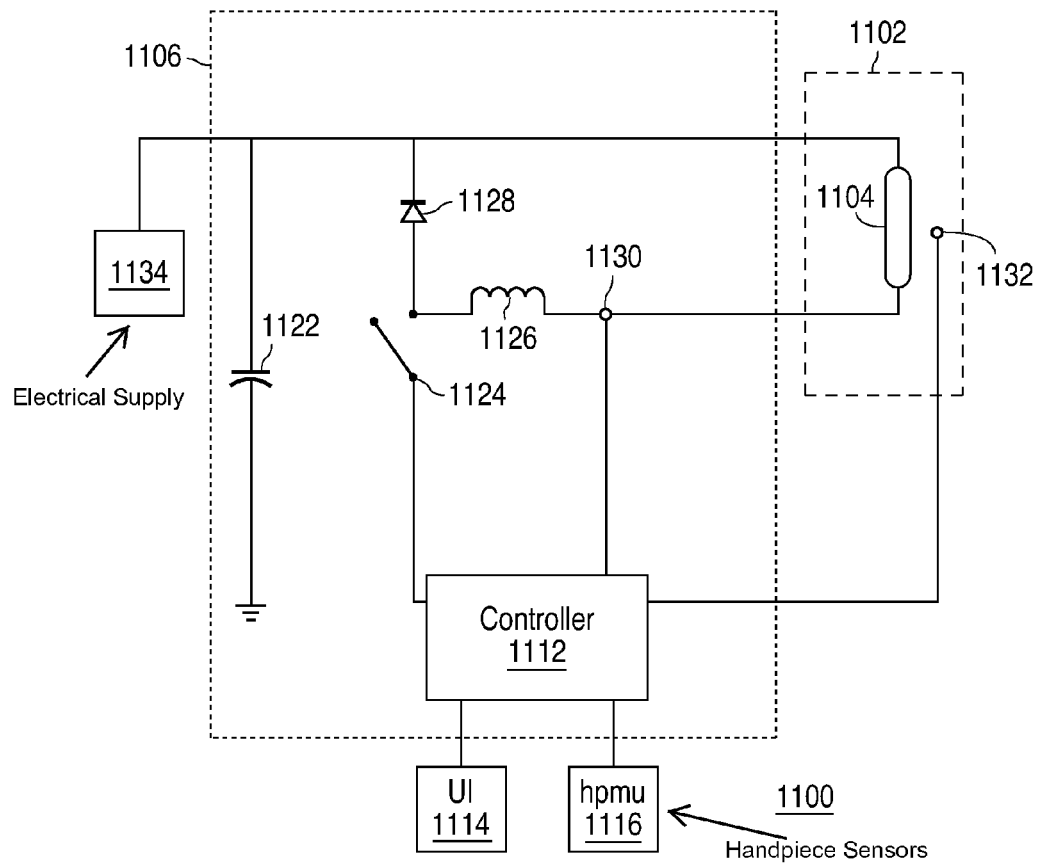
FIG. 11 shows a embodiment of a system herein.

FIG. 11 shows a detailed view of an embodiment of system herein. Specifically, FIG. 11 shows a view of a high voltage power supply 1106 which could be used to drive the filament lamp 1104 in the handpiece 1102 in the manner described above in connection with FIG. 9. As shown in detail in the U.S. provisional application Ser. No. 60/540,981, filed Jan. 30, 2004, entitled SYSTEM AND METHOD FOR FLEXIBLE ARCHITECTURE FOR DERMATOLOGICAL TREATMENTS UTILIZING MULTIPLE LIGHT SOURCES, AND FILAMENT LIGHT SOURCE TO BE USED IN COMBINATION WITH THE SYSTEM AND METHOD FOR FLEXIBLE ARCHITECTURE FOR DERMATOLOGICAL TREATMENTS, which is incorporated herein by reference, the power supply is very controllable and can operate to switch between and drive different types of light sources. In one embody the power supply uses a controlled chopper circuit with an inductive filter element 1126, operating in a pulse width modulated controlled current mode (in which the current is controlled and the voltage is determined by the device impedance and the impedance of the filter). Power supply 1106 could be also operated in a pulse width modulated controlled voltage mode (in which the voltage is controlled and the current is not controlled) or in a controlled power mode (in which the voltage and/or current are controlled in a manner resulting in controlled power).

In an embodiment herein, the controller of the power supply 1112 receives signals originating from the user interface 1114 and possibly sensors 1116 in the hand piece management unit which can determine when the handpiece 1102 has been removed from a seated position, and based on these signals determines how to drive the filament lamp when the user activates the filament lamp, by stepping on a foot pedal switch for example.

The operation of the power supply will be described in the context of the situation where a user has removed the handpiece 1102 from a hand piece management unit, and initiated the activation of the filament lamp 1104 of the hand piece 1102. In this situation when the hand piece 1102 is removed from a resting or seated position and activated the filament lamp, the operation described above will be performed.

The energy storage capacitor 1122 is charged to by the main electrical supply 1134 to a level allowing the desired energy to be delivered without unacceptable lamp voltage droop, where driving the filament lamp, at the desired current. When switch 1124 is closed current ramps up current through the filament lamp 1104, inductor 1126, and switch 1124. When the appropriate output power or current is reached, the controller 1112 opens the switch 1124 and the current now diverts to the diode 1128. When the current flow or output power drops to an appropriate level the controller 1112 again turns on the switch 1124 and the cycle repeats until a pulse is complete.

This toggling of switch 1124 on and off during a treatment exposure results from the photodiode 1132, or use of a voltage sensing circuit, determining that the optical power has reached a maximum value, and in response the controller opens the switch, and when the optical power drops to a low target level the switch closes, which increase the current through the filament lamp. It should be noted that as discussed in connection with FIG. 9, one embodiment operates with a central target for optical power of around 16 W, however, the power supply operation could be adapted such that the power supply drove the filament to output both varying amounts of power and varying treatment exposures. Also the current sensor 1130 and photodiode 1132 can be used independently or in concert to control the optical power delivered to skin.

Figure 12:
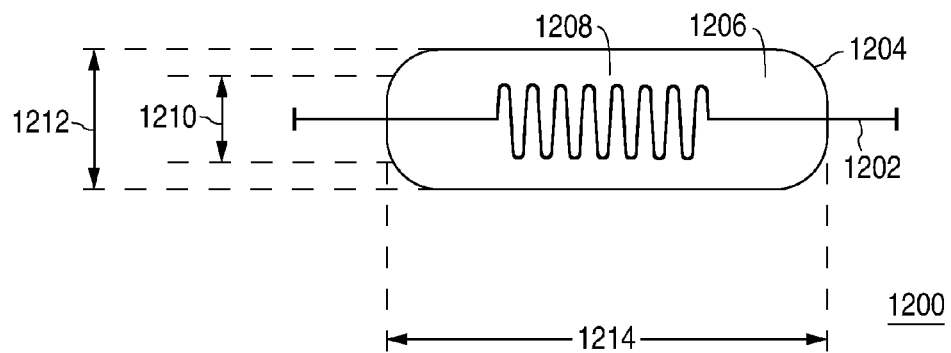
FIG. 12 shows an embodiment of a filament lamp of the present system.

FIG. 12 shows an embodiment of lamp herein 1200. Aspects of suitable QTH lamps are described above. As discussed above it is important to be able to obtain sufficient optical power from the lamp in order to obtain the desired heating. Many previously available filament lamps are of relatively large dimensions relative to a treatment exposure area, and it can be very difficult to utilize these previous designs to obtain the desired heating. To achieve higher power the dimensions of a filament lamp in an embodiment herein have been changed relative to previously available lamps. The elements of a lamp 1200 illustrated in FIG. 12 illustrate significant dimensions of the lamp. The lamp includes a tungsten filament 1202. A portion of the filament 1202 is disposed in a quartz tube 1204, and the area inside the tube is filled with a gas 1206 which can include halogen. The portions of the filament that are outside of the tube 1204 can be partially sealed in tabs of the quartz tube which are not shown, and these tabs could be used to physically and electrically coupling the lamp 1200 with the other elements of the system. In one embodiment the length of the tube 1204 is about 2.4 inches (60 mm). In one embodiment the diameter of the filament is 0.75 mm, but a range of different thicknesses could be used. A center portion 1208 of the filament 1202 is formed in to a helical coil shape. In one embodiment the helical coil shape has a diameter 1210 which is approximately 6 mm. In one embodiment the tube diameter 1212 is approximately 10 mm. The ratio of the diameter of the tube 1204 and the diameter of the helical coil 1208 is 10:6. This ratio is very different that previous filament lamps where a ration of greater than 10:1 is very common. Generally, filament lamps utilize air-cooling. Where air cooling is used it is important to maintain a sufficient area for cooling the lamp, and generally one way of ensuring sufficient area is to maintain relatively large tube diameter relative to the diameter of the coil. Generally as the ratio of the tube diameter to the helical diameter gets below about 5:1 it is believed that air cooling will no longer be sufficient to cool the lamp, when it is driven at currents which are necessary to output the optical power required for the thermal treatments described herein, and as the ratio becomes less (for example the 2:1) as is the case described in connection with the lamp 1200 shown in FIG. 12 the cooling issues must be addressed, and the required energy fluences are obtained.

Given the ratio of the diameter of the tube to relative to the coil in the embodiment of the lamp discussed above, and the amount of current which is used to generate a treatment exposure, traditional air cooling would not be sufficient to keep the lamp cool enough so that it would not become damaged and fail. Thus, the flow tube and liquid cooling discussed above is utilized to cool the lamp.

It should be recognized that the filament light source discussed herein is advantageous over some other light sources in that it is relatively inexpensive, and outputs a broad spectrum of light in the NIR range. At present flashlamps do not appear to provide as good a source for producing a broad range of power in the NIR spectrum, but some flashlamps might be suitable to produce such a range of light, and could be considered for use in a system for providing deep thermal heating.

While various embodiments of the present invention have been described above, it should be understood that they have been presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Thus, the present invention should not be limited by any of the above-described exemplary embodiments, but should be defined only in accordance with the following claims and their equivalents.

What is claimed is:

1. A method for tightening skin, comprising:
    generating a broadband spectrum of near infrared radiation with a filament light source, said broadband spectrum continuously covering a range of at least 1050 nm to 1850 nm;
    filtering out radiation from the broadband spectrum below 1050 nm and above 1850 to produce a spectrum having a wavelength band consisting essentially of radiation covering 1050 nm and 1850 nm;
    placing a transmissive material in contact with an upper surface of the skin to be treated;
    transmitting the filtered radiation generated by the light source through the transmissive material to the skin;
    cooling the transmissive material; and
    wherein the radiation transmitted to the skin and the cooling of the transmissive material create an inverted temperature profile in the skin, such that the upper surface of the skin is cooler than an area of skin below the upper surface, and wherein the radiation is transmitted to the skin for a continuous period of time of between approximately 1.2 (one and two-tenths) seconds and 5 (five) seconds and provides for heating a volume of dermis in the skin, which is at a depth of between 1 mm to 5 mm below the upper surface of the skin, to a treatment temperature which is at least 50° C. while maintaining the regions of the dermis at depths shallower than 1 mm at temperatures below the treatment temperature, wherein the skin is tightened as a result of heating the volume of dermis.

2. The method of claim 1, wherein the treatment temperature is at least 60° C.

3. The method of claim 1, wherein transmitting light energy from the light source includes applying a plurality of electrical current pulses to the filament of the filament light source, wherein a first pulse of the plurality of the electrical current pulses is the longest pulse of the plurality of pulses and operates to bring the filament to a temperature which results in the filament light source emitting light.

4. The method of claim 1, wherein transmitting light energy from the light source the transmitting step includes:
    applying a plurality of electrical pulses to the filament of the filament light source;
    sensing light produced by the filament; and
    when a power of the light produced by the filament drops below a first power level, applying a pulse of electrical current to the filament.

5. The method of claim 1 further comprising, starting the cooling of the transmissive material prior to transmitting radiation to the skin.

6. The method of claim 1, further comprising,
   continuing the cooling of the transmissive material for a predetermined time period after the termination of the transmission of radiation to the skin;
   providing a notification signal to the user signaling the end of the predetermined time period; and
   maintaining contact between the transmissive material and the skin until after the notification signal is provided.

7. The method of claim 6, wherein the filament light source is provided on a handpiece, wherein the method includes providing a visual indication on the handpiece, wherein providing the notification signal includes discontinuing the visual indication after the end of the predetermined time period.

8. The method of claim 6 wherein providing the notification signal includes sounding an auditory signal after the end of the predetermined time period.

9. The method of claim 5 further comprising, continuing the cooling of the transmissive material during the transmission of radiation to the skin.

\* \* \* \* \*